(12) United States Patent
Brown et al.

(10) Patent No.: US 7,596,997 B2
(45) Date of Patent: *Oct. 6, 2009

(54) METHODS AND APPARATUS FOR AN IN-FLIGHT PRECIPITATION STATIC SENSOR

(75) Inventors: Arlene M. Brown, Seattle, WA (US); Grant J. Erickson, Enumclaw, WA (US); Joe Heeter, Sammamish, WA (US); David W. Kwolek, Renton, WA (US); Robert Steinle, Seattle, WA (US); Kari L. Stromsland, Seattle, WA (US)

(73) Assignee: The Boeing Company, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/120,840

(22) Filed: May 15, 2008

(65) Prior Publication Data

US 2008/0246490 A1 Oct. 9, 2008

Related U.S. Application Data

(63) Continuation of application No. 11/615,275, filed on Dec. 22, 2006, now Pat. No. 7,373,814.

(51) Int. Cl.
*G01W 1/00* (2006.01)
(52) U.S. Cl. .................................................. 73/170.17
(58) Field of Classification Search ............ 73/170.17, 73/170.26; 340/580; 244/134
See application file for complete search history.

(56) References Cited

U.S. PATENT DOCUMENTS

| 4,190,088 | A | 2/1980 | Lalikos et al. |
| 4,259,989 | A | 4/1981 | Lalikos et al. |
| 5,443,912 | A | 8/1995 | Olson |
| 6,295,366 | B1 | 9/2001 | Haller et al. |
| 6,375,120 | B1 | 4/2002 | Wolnek |
| 7,373,814 | B1 * | 5/2008 | Brown et al. ............. 73/170.17 |

* cited by examiner

*Primary Examiner*—Jewel Thompson
(74) *Attorney, Agent, or Firm*—Yee & Associates, P.C.; Brett L. Halperin

(57) ABSTRACT

A precipitation static sensor includes a bottom flexible dielectric layer (e.g., a layer of urethane tape) configured to be attached to a wing or other external surface of an aircraft, a flexible conductive layer (e.g., a layer of aluminum tape) formed over a portion of the first flexible dielectric layer, and a conductor (such as a twisted-pair wire) coupled to the flexible conductive layer. A top flexible dielectric layer is formed over a portion of the bottom dielectric layer and a portion of the flexible conductive layer, thus forming an exposed detector region. In accordance with a further embodiment, multiple such precipitation static sensors are used and coupled to a meter device (e.g., a picoammeter), which may also be coupled to a data acquisition and display for providing a visual indication of the charge accumulated by the precipitation static sensors.

20 Claims, 2 Drawing Sheets

METHODS AND APPARATUS FOR AN IN-FLIGHT PRECIPITATION STATIC SENSOR

This application is a continuation application of U.S. patent application Ser. No. 11/615,275, entitled "Methods and Apparatus for an In-Flight Precipitation Static Sensor," filed on Dec. 22, 2006 now U.S. Pat. No. 7,373,814.

TECHNICAL FIELD

The embodiments described herein generally relate to aircraft sensors, and more particularly relate to in-flight precipitation static sensors.

BACKGROUND

During flight, an aircraft is subject to the impingement of particles on its various external surfaces, leaving charge on the aircraft due either to triboelectric processes or charged particle interactions, particularly while flying through rain, snow, dust, or clouds. This can lead to charge build up, referred to as precipitation static or "p-static," which is typically discharged using some form of discharge device. The accumulation and discharge of p-static can lead to disruptions in RF radio communication and other deleterious effects.

Traditionally, a pilot flying through the environment merely determines whether various electronic components work qualitatively, without a quantitative measure of the level of p-static. Conventional static wicks may used to assess the environment, but such systems do not provide detailed quantitative information.

Furthermore, it has been a trend for the Federal Aviation Authority (FAA) to promulgate increasingly-stringent p-static standards. As a result, new certification approaches require better and more quantitative measurements of p-static charge rate during flight.

Accordingly, it is desirable to provide sensitive p-static sensors that are manufacturable and can withstand the environmental extremes experienced by external aircraft surfaces. Furthermore, other desirable features and characteristics of the p-static sensors will become apparent from the subsequent detailed description and the appended claims, taken in conjunction with the accompanying drawings and the foregoing technical field and background.

BRIEF SUMMARY

A precipitation static sensor in accordance with one embodiment generally includes a bottom flexible dielectric layer (e.g., a layer of urethane tape) configured to be attached to a wing or other external surface of an aircraft, a flexible conductive layer (e.g., a layer of aluminum tape) formed over a portion of the first flexible dielectric layer, and a conductor (such as a twisted-pair wire) coupled to the flexible conductive layer. A top flexible dielectric layer is formed over a portion of the bottom dielectric layer and a portion of the flexible conductive layer, thus forming an exposed detector region.

In accordance with a further embodiment, multiple such precipitation static sensors are used and coupled to a meter device (e.g., a picoammeter), which may also be coupled to a data acquisition and display for providing a visual indication of the charge accumulated by the precipitation static sensors. Appropriate filters may be coupled to the sensors to reduce the effects of aircraft-generated RF noise.

BRIEF DESCRIPTION OF THE DRAWINGS

Various embodiments will hereinafter be described in conjunction with the following drawing figures, wherein like numerals denote like elements.

DETAILED DESCRIPTION

The following detailed description is merely exemplary in nature and is not intended to limit the described embodiments or the application and uses of the described embodiments. Furthermore, there is no intention to be bound by any expressed or implied theory presented in the preceding technical field, background, brief summary or the following detailed description. For the sake of brevity, conventional techniques, components, and principles related to aeronautics, sensors, static electricity, and digital acquisition systems are not described in detail herein.

The terms "first," "second," "third," "fourth" and the like in the description and the claims, if any, may be used for distinguishing between similar elements and not necessarily for describing a particular sequential or chronological order. These terms, so used, are interchangeable under appropriate circumstances. The embodiments of the invention described herein are, for example, capable of use in sequences other than those illustrated or otherwise described herein. The terms "comprise," "include," "have" and any variations thereof are used synonymously to denote non-exclusive inclusion. The terms "left," right," "in," "out," "front," "back," "top," "bottom," and other such directional terms are used to describe relative positions, not necessarily absolute positions in space. The term "exemplary" is used in the sense of "example," rather than "ideal."

Figure 1:
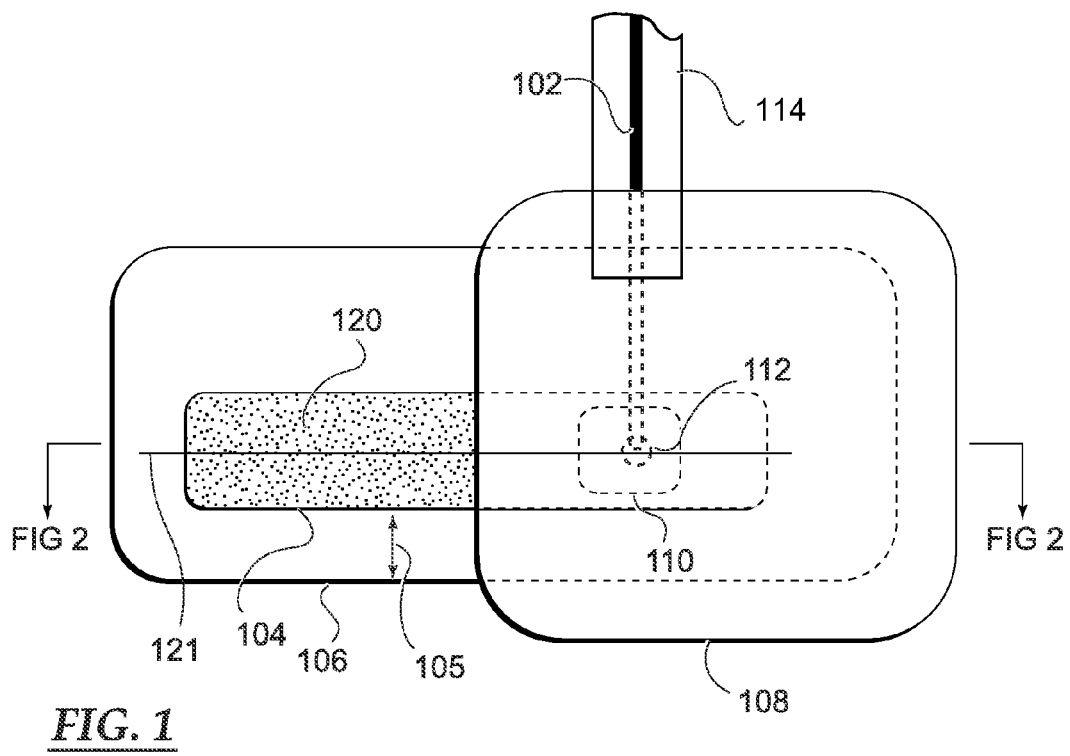
FIG. 1 is a top view of a p-static sensor in accordance with one embodiment.
Figure 2:
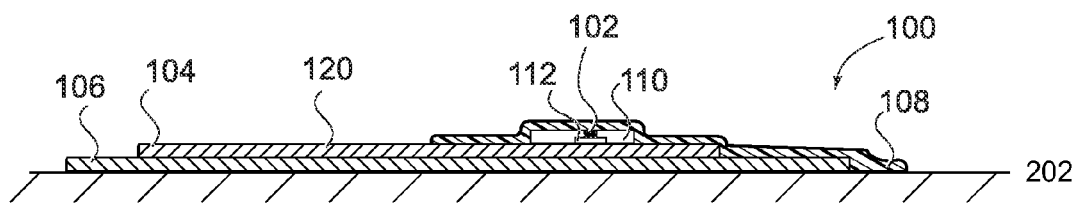
FIG. 2 is a cross-sectional view of section A-A of the p-static sensor shown in FIG. 1.

FIG. 1 is a conceptual top view of an exemplary precipitation static sensor 100 (alternatively referred to as a "p-static sensor," or simply "sensor"), and FIG. 2 is a cross-sectional view of the same p-static sensor through cross-section A-A of FIG. 1. These figures are not necessarily drawn to scale, thus the thicknesses and geometries of the various layers in the figures are not intended as limitations.

In general, sensor 100 includes a conductive layer 104 positioned between two dielectric layers 106 and 108, where only a portion of conductive layer 104 and bottom dielectric layer 106 are covered by top dielectric layer 108, thereby forming an exposed detector region 120. Additional intervening layers such as adhesive layers and the like may also be present, but for the purposes of clarity are not included in these figures. Exposed detector region 120 consists of a surface area of conductive layer 104 configured to accumulate p-static charge produced by impinging particles during flight. This charge build up (or "charge rate") can be sensed and displayed for use by the pilot or other personnel, as described in further detail below.

A conductor 102 (e.g., a wire) is connected to or otherwise electrically coupled to conductive layer 104. In the illustrated embodiment, one conductive patch 112 (e.g., a small copper patch) is provided between the end of conductor 102 and conductive layer 104, and another conductive patch 110 is formed over the end of conductor 102. Patches 112 and 110 are configured to assist in mechanically and electrically securing conductor 102 to conductive layer 104. Conductor 102 may, for example, include a twisted pair consisting of two wires—one of which is soldered or otherwise electrically coupled to conductive layer 104, and another that is terminated and connected to the shield of the twisted pair assembly. A protective tape layer 114 may be placed over conductor 102 as well.

Bottom dielectric layer 106 and top dielectric layer 108 may include any material or combination of materials that provide suitable insulation between conductive layer 104 and the surrounding environment and structures. That is, bottom dielectric layer 106 suitably insulates conductive layer 104 from aircraft structure 202, and top dielectric layer 108 suitably insulates a portion of conductive layer 104 from the surrounding environment (while helping to protect and secure conductor 102).

Bottom dielectric layer 106 is configured to be attached (e.g., bonded via an adhesive or the like) to a wing or other external structure 202 of an aircraft. Accordingly, it is desirable for layers 106, 104, and 108 to be flexible in the sense that they substantially conform to any curvature of external surface 202. Furthermore, to the extent that sensor 100 is to be used in an environment that is subject to fast-moving air and particles, it is desirable for these layers to be relatively robust.

In this regard, a variety of materials may be used for layers 108 and 106, including various elastomeric insulating materials. In one embodiment, for example, layers 108 and 106 both consist of a relatively thin layer of polyurethane. In a particular embodiment, a polyurethane tape (which may have one or more adhesive sides) is used. A variety of polyurethane tapes are acceptable, including, for example, 3M Polyurethane Protective Tape 8681HS manufactured by 3M, Inc, which is relatively weather-resistant, and has an approximate as-applied thickness of 0.012-0.016 in.

Depending upon the severity of the charging environment and susceptibility to noise, an additional layer (not shown) of fluoropolymer film may be used under the 106 bottom and/or 108 top urethane layer to provide additional dielectric separation while minimizing the effects of aerodynamic drag. In one embodiment, this additional layer is larger than detector area 120, typically by at least 0.0125 in., but smaller than the corresponding urethane layer. Example materials for this additional layer include PTFE film manufactured by CS Hyde Co. (#15-10S-2-5) and Skived PTFE (Teflon) Tape Silicone Adhesive having an as-applied thickness of about 0.010 in. plus 0.0015 in. adhesive. Other materials may be used, depending upon the nature of the location of the sensor on the aircraft surface.

It is also desirable for conductive layer 104 to be substantially flexible to conform to structure 202 of the aircraft. In one embodiment, for example, conductive layer 104 comprises a relatively thin layer of aluminum or an aluminum alloy. In a specific embodiment, conductive layer 104 is in the form of a tape comprising a viscoelastic polymer layer bonded to an aluminum constraining layer, such as the 3M Aluminum Vibration Damping Tape 434 manufactured by 3M, inc. This tape has an approximate thickness of 7.0-8.0 mils as applied.

Metals and dielectrics other than those shown in the illustrated embodiments may be used for the various layers, provided they are capable of surviving within the aircraft's flight environment. Acquiring data using different materials may assist in distinguishing the source of the charging—i.e., triboelectric verses charged particles. In an alternate embodiment, the bottom flexible dielectric layer may be omitted and the flexible conductive layer detector applied directly to the aircraft.

Figure 3:
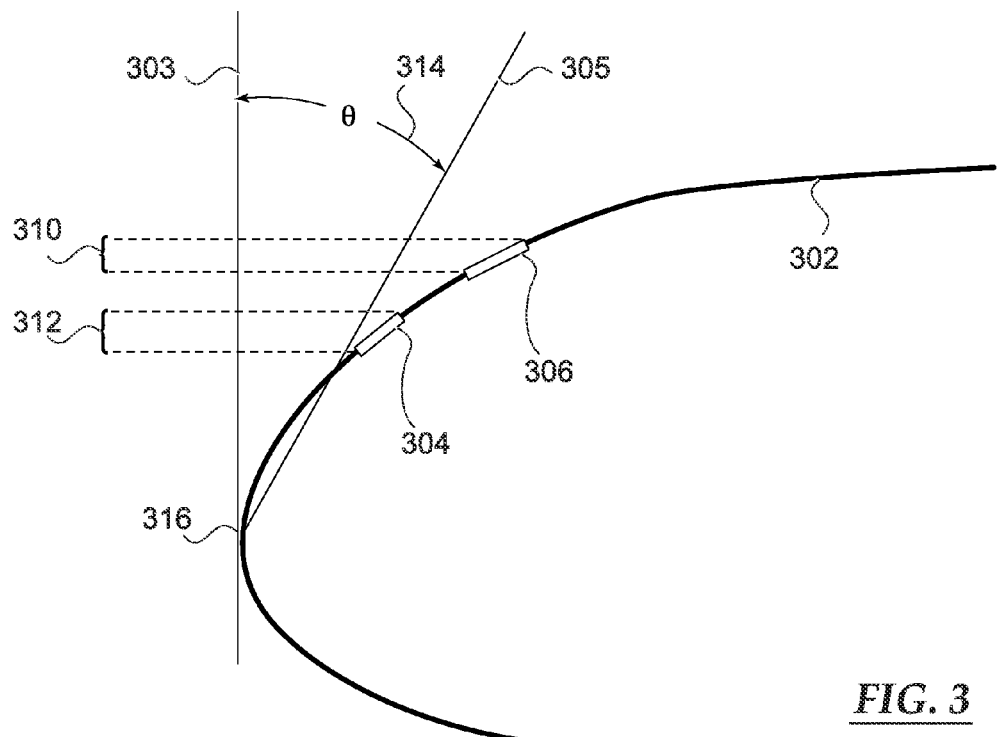
FIG. 3 is a conceptual side view of a wing profile with two sensors positioned at various angles with respect to the leading edge.

One or more sensors 100 may be included on various external surfaces of the aircraft. Wing surfaces, for example, provide an advantageous location to measure p-static, and in one embodiment multiple sensors (e.g., 2, 4, or more) are placed at various locations along a wing. Referring to the side view shown in FIG. 3, for example, two p-static sensors 304 and 306 are placed at different points along wing profile or contour 302. The free-stream flow direction, during flight, is generally left to right in this figure, and conforms in a known way to contour 302.

Sensor 306 has a projected area 310 (i.e., a projection of the area of sensor 306 onto a vertical plane 303), and sensor 304 has a projected area 312. Given that the sensor chord lengths are roughly equal and because sensor 306 is higher along profile 302, its projected area may be less than that of sensor 304 if the un-pictured dimensions of sensor 304 and 306 are equivalent. Given that the sensor chord lengths are roughly equal, if the un-pictured dimensions of sensor 302 and 306 are different, the projected area 310 and 312 may or may not be equivalent. The placement of these sensors may be described using any suitable convention. In the illustrated embodiment, an angle 314 (θ) is defined between vertical line 303 through leading edge 316 of the wing and line 305 leading from leading edge 316 through the relevant sensor 304, 306 (i.e., the bottom edge of the exposed detector region). Thus, the position of each sensor 304, 306 may be specified by angle θ. In an exemplary embodiment, multiple sensors are placed at various locations on wing profile 302 at angles 314 ranging from 10 degrees to 70 degrees. In a particular embodiment, sensors are placed at 10 degrees, 25 degrees, 50 degrees, and 68 degrees. It will be appreciated that these angles will vary depending upon the shape of wing contour 302, and are meant merely to give one example sensor placement rather than to be a limitation on the range of possible embodiments.

Referring again to FIG. 1, exposed detector region 120 may have any suitable dimensions and shape, but in one embodiment is a rectangle measuring about 3.0×1.0 inches (3 square inches total area), wherein the total area of conductive layer 104 is about twice that (i.e., 6.0×1.0 inches).

Exposed detector region 120 has a major axis 121 (in this illustration, the horizontal axis). In accordance with one embodiment, sensor 100 is positioned on the external surface 202 of the aircraft such that major axis 121 is substantially perpendicular to the anticipated free-stream flow direction. Thus, in the case of sensors 304 and 306 placed on wing contour 302 such as that shown in FIG. 3, the sensors may be oriented such that the major axis of their respective exposed detector regions (not shown in FIG. 3) are perpendicular to the free-stream flow direction, which is generally left to right in this figure. By using sensors in multiple locations on the wing that are subject to different levels of charging, it allows the subsequent analysis to validate the measurement technique. The sensor closest to the leading edge will typically exhibit the greatest charge rate. When assessing charging rates for other aircraft parts, the orientation, size, and detector size will vary.

The size and shape of the various layers that make up sensor 100 may vary depending upon application. In one embodiment, where sensor 100 is applied to a wing surface, top dielectric layer 108 is generally rectangular with an area of 4.75×5.56 inches, and bottom dielectric layer 106 is rectangular with an area of 8.0×4.0 inches, but for a location where charging is less severe, a larger size may be used, e.g., 13.0×3.6 inches. Layers 104, 106 and 108 may have rounded edges or corners (e.g., ¼" round corners) as shown, or may have any suitable shape. In one embodiment, layer 104 has an area that is substantially smaller than the area of layer 106, and is positioned such that a margin 105 is formed between the perimeter of layer 104 and the perimeter layer 106, wherein the margin is sufficient to maintain charge on the sensor—in a particular embodiment, approximately 0.75 inches. These dimensions and geometries are merely exemplary, however, and are not intended to limit the range of possible embodiments.

While the illustrated embodiment describes sensors attached to various aerodynamic surfaces of the aircraft, the sensors may be incorporated into removeable mounting brackets, posts, and the like. Such removeable sensors may be used along the fuselage, on door access hatches, and the like, and are preferably placed where their loss would not create a safety hazard.

Having thus given an overview of the various components of an exemplary sensor, a method of forming the sensor will now be described in conjunction with FIGS. 1 and 2. First, a layer of tape, such as adhesive-backed metallic foil tape (not shown) may be applied on structure 202 to provide a suitable surface in the areas where the sensors are to be formed. Any bubbles or seams are avoided. The surface of structure 202 may first be cleaned using, for example, a suitable solvent prior to application of the tape. Furthermore, the surface of the tape may be abraded (e.g., using abrasive paper or cloth) and cleaned to prepare it for bonding to subsequent layers. This tape layer is preferably electrically grounded to the aircraft.

A segment of polyurethane tape is applied to the prepared surface to form bottom layer 106. An adhesion promoter layer such as 3M Adhesion Promoter 86A (not shown) may be used to assist in adhesion of this layer. Any air bubbles that form during this step are preferably removed. A layer of aluminum tape is then applied to a region within bottom layer 106 to form conductive layer 104. Again, an adhesion promoter may be used to assist in bonding. The desired exposed detector region 120 is then masked off to protect it temporarily during subsequent processing, and conductive layer 104 is abraded lightly.

Conductor 102 is soldered or otherwise attached to small copper patch 112, which has conductive adhesive on one side. Small copper patch 112 is then applied, adhesive side down, to conductive layer 104 where it will be completely covered by top dielectric layer 108 such that the attached conductor 102 lays in the direction of airflow over the aerodynamic surface. Small copper patch 112 is then applied, adhesive side down, over copper patch 102. Suitable rubbing pressure is applied to the patches to ensure good electrical contact. Conductor 102 may alternately be attached to conductive layer 104 by welding or soldering directly to the metallic layer.

Next, top layer 108 is formed by applying another layer of polyurethane tape on top of copper patch 112, bottom layer 106, and a portion of conductive layer 104, thereby holding conductor 102 and patches 110, 112 in place. Conductor 102 is further secured along structure 202 of the aircraft using a tape 114.

Figure 4:
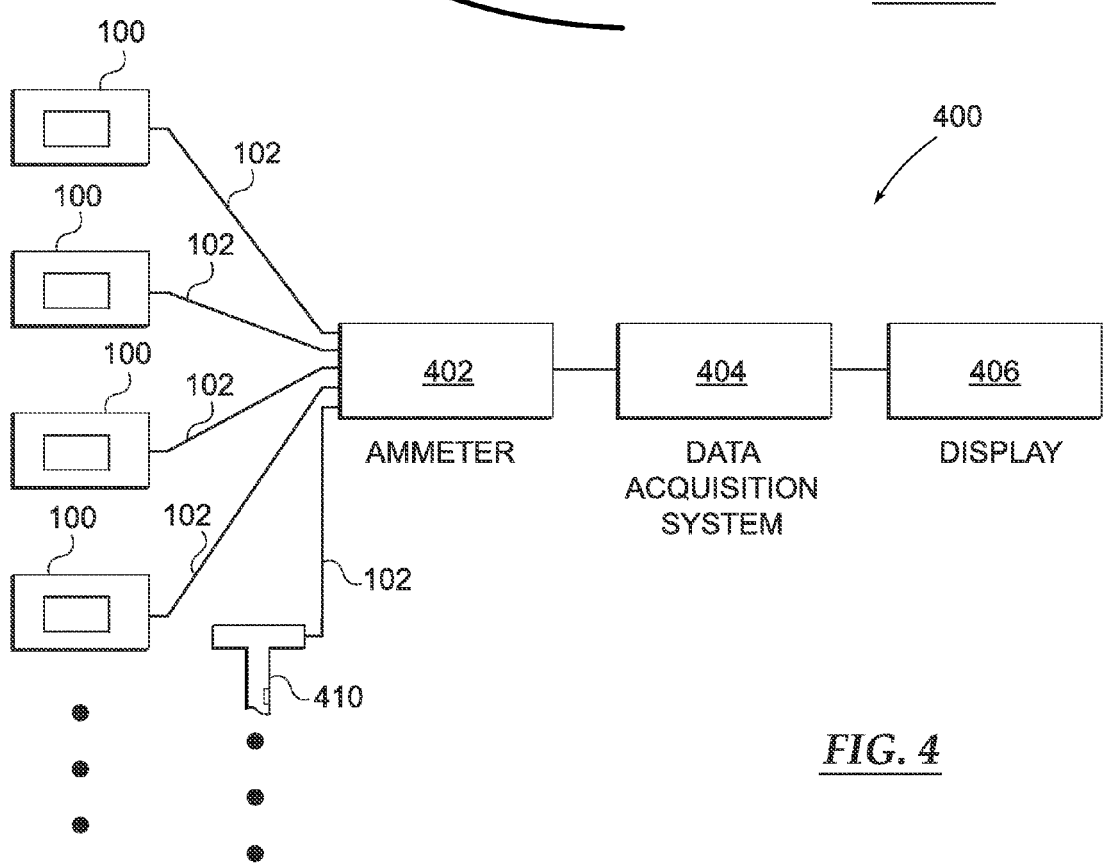
FIG. 4 is a block diagram of a p-static sensor system in accordance with one embodiment.

FIG. 4 depicts a conceptual block diagram of a system 400 in accordance with one embodiment, and includes a number of sensors 100 coupled to a meter device (e.g., an ammeter) 404 via conductors 102. Conductors 102 are suitably routed from sensors 100 to the fuselage of the aircraft, where meter device (or devices) 402 is preferably housed.

System 400 may also include one or more probe sensors (or other types of sensors) 410 located at various positions on the aircraft. For example, a probe sensor 410 may be located in the near free stream air flow such that it is configured to obtain precipitation charging data in the respective precipitation charging environments. Such probes may be located, for example, near a door, hatch, nose, or the like.

Probe sensor 410 has the same general purpose as sensors 100 (i.e., collecting charge as the airplane flies through p-static charging conditions), but probe sensor 410 extends out into the airstream away from aircraft and is thus able to collect charge in what is referred to as "near freestream" conditions. Airflow over the wing leading edge affects the collection efficiency of wing-mounted sensors, such that lighter and smaller particles are deflected from the sensors. On sensors farther back from the leading edge, fewer particle impacts and lower charging rates will be recorded. Because probe-mounted sensor 410 is in near freestream conditions, its readings provide a benchmark with which readings from sensors 100 may be compared.

Meter device 402 is configured to produce a signal (e.g., a current signal) that is responsive to and correlated to the magnitude of p-static charge that builds up on sensors 100 during operation. Although one meter device 402 is illustrated (e.g., a meter with multiple inputs), multiple meter devices 402 may be employed—one for each of the sensors 100.

The signals from sensors 100 may be filtered (e.g., to reduce aircraft-generated RF noise) prior to meter device 402 using one or more filters (not shown). Meter devices 402 having the appropriate sensitivity, such as a picoammeter, may be used. In one embodiment, measurements are acquired at 10 samples per second, with four significant figures, and a picoammeter range set to 2 micro-amps.

A data acquisition system 404 may be used to acquire data in real time from meter device 402. That is, data acquisition system 404 receives data from the multiple sensors 100 through ammeter 402 (or multiple ammeters 402) and processes the data for further analysis. The resultant data may then be displayed to the pilot or other personnel using a display 406. Display 406 may be a simple single-line text display, or may be a two-dimensional display for presenting a quantitative and/or qualitative representation of the p-static charge sensed by sensors 100. A real-time graphical display, strip chart recorder, or the like may be used for documenting the meter readings. Furthermore, the data from sensors 100 may be correlated with other data produced during the flight, such as altitude, speed, slat angle, weather conditions, pressure, angle-of-attack, latitude-longitude coordinates, and the like. Instrumentation that provides particle count, particle concentration and static wick discharge data aids subsequent analysis. Various embodiments might include software modules for providing real-time in-flight analysis of the available data.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof.

The invention claimed is:

1. A precipitation static sensor comprising:
   a first dielectric layer configured to be attached to an external surface of an aircraft;
   a conductive layer formed over a portion of the first dielectric layer;
   a conductor having a first end coupled to the conductive layer; and
   a second dielectric layer formed over a portion of the first dielectric layer, the first end of the conductor, and a portion of the conductive layer, such that the conductive layer includes a detector region.

2. The precipitation static sensor of claim 1, wherein the first dielectric layer comprises a layer of urethane.

3. The precipitation static sensor of claim 1, wherein the second dielectric layer comprises a layer of urethane.

4. The precipitation static sensor of claim 1, wherein at least one of the first dielectric layer and second dielectric layer comprises a tape.

5. The precipitation static sensor of claim 1, wherein the conductive layer comprises aluminum.

6. The precipitation static sensor of claim 5, wherein the conductive layer comprises an aluminum tape having an adhesive side coupled to the first dielectric layer.

7. The precipitation static sensor of claim 1, wherein the conductor comprises a twisted-pair comprising a shield, a first wire, and a second wire, and wherein the first wire is coupled to the metallic layer, and the second wire is connected to the shield.

8. The precipitation static sensor of claim 1, further comprising a conductive patch connected to the conductor and the conductive layer.

9. The precipitation static sensor of claim 1, wherein the detector region is exposed outside the aircraft and wherein the detector region has a major axis that is substantially perpendicular to an anticipated free-stream flow.

10. The precipitation static sensor of claim 1, wherein the conductive region has a first area that is substantially smaller than a second area of the first dielectric region, and wherein the conductive region is positioned such that a margin is formed between a perimeter of the conductive region and a perimeter of the first dielectric region, wherein the margin no less than approximately 0.75 inches.

11. A method for forming a precipitation-static sensor on an external surface of an aircraft, comprising:
    forming a first dielectric layer on the external surface of the aircraft;
    forming a conductive layer over a portion of the first dielectric layer;
    attaching a first end of a conductor to the conductive layer; and
    forming a second dielectric layer over a portion of the first dielectric layer, the conductor, and a portion of the conductive layer, such that the conductive layer includes detector region.

12. The method of claim 11, wherein forming the first dielectric layer includes applying a layer of urethane tape.

13. The method of claim 11, wherein forming the conductive layer includes applying a layer of aluminum tape.

14. The method of claim 11, wherein forming the second dielectric layer includes applying a layer of urethane tape.

15. The method of claim 11, further including coupling a second end of the conductor to an ammeter.

16. The method of claim 11, wherein forming the second dielectric layer includes forming the second dielectric layer such that the detector region has a major axis that is substantially perpendicular to an anticipated free-stream flow for the external surface of the aircraft.

17. A system for measuring in-flight precipitation static experienced by an aircraft, the system comprising:
    at least one precipitation static sensor coupled to an external surface of the aircraft, the precipitation static sensor comprising: a first dielectric layer attached to an external surface; a conductive layer formed over a portion of the first dielectric layer; a conductor having a first end coupled to the conductive layer; and a second dielectric layer formed over a portion of the first dielectric layer, the first end of the conductor, and a portion of the conductive layer, such that the conductive layer includes detector region;
    a meter device communicatively coupled to the conductor, the meter device configured to produce a current responsive to a charge accumulated by the at least one precipitation static sensor.

18. The system of claim 17, further including a data acquisition coupled to the meter device, and a display coupled to the data acquisition system, wherein the display is configured to provide a visual indication of the charge accumulated by the at least one precipitation static sensor.

19. The system of claim 17, wherein the at least one precipitation static sensor comprises a plurality of precipitation static sensors positioned at multiple locations along a wing of the aircraft.

20. The system of claim 19, wherein each of the plurality of precipitation static sensors has a major axis that is substantially perpendicular to a free-stream flow direction of the external surface.

* * * * *